United States Patent [19]
Dorsey, III

[11] Patent Number: 5,586,977
[45] Date of Patent: Dec. 24, 1996

[54] QUICK DISCONNECT FITTING FOR COUPLING INTERCHANGEABLE PROBE TIP TO LAPAROSCOPIC INSTRUMENT

[75] Inventor: James H. Dorsey, III, Delray Beach, Fla.

[73] Assignee: C.R. Bard, Inc., Murray Hill, N.J.

[21] Appl. No.: 286,949

[22] Filed: Aug. 8, 1994

Related U.S. Application Data

[63] Continuation of Ser. No. 989,109, Dec. 11, 1992, abandoned, which is a continuation-in-part of Ser. No. 470,771, Jan. 26, 1990, Pat. No. 5,188,591.

[51] Int. Cl.$^6$ ............................................. A61M 5/00
[52] U.S. Cl. ............................ 604/264; 604/30; 604/33; 604/35; 604/283; 128/912; 285/921
[58] Field of Search ........................... 604/35, 241, 243, 604/283, 902, 275, 264, 250, 240, 40, 43, 39, 30; 285/921; 128/912

[56] References Cited

U.S. PATENT DOCUMENTS

| | | |
|---|---|---|
| 738,503 | 9/1903 | Waters ............................ 285/921 |
| 1,538,007 | 5/1925 | Schellin . |
| 3,484,121 | 9/1966 | Quinton . |
| 4,248,589 | 2/1981 | Lewis . |
| 4,257,416 | 3/1981 | Prager . |
| 4,451,069 | 5/1984 | Melone . |
| 4,484,769 | 11/1984 | Lacey . |
| 4,580,816 | 8/1986 | Campbell et al. . |
| 4,592,749 | 6/1986 | Ebling et al. ..................... 604/283 |
| 5,049,071 | 9/1991 | Davis et al. . |

Primary Examiner—Randall L. Green
Assistant Examiner—Mark Bockelman
Attorney, Agent, or Firm—Darby & Darby

[57] ABSTRACT

A medical device is herein described for provision of a pressurized fluid through interchangeable probes. In the preferred embodiment of this medical device, the interchangeable probes are mounted to a handset having a quick disconnect/reconnect mount which not only permits rapid attachment and removal of such probes to the handset, but also the freedom of change in orientation of the probe relative to the handset to accommodate variable condition/requirements of an operative procedure and clinician preferences. In the preferred embodiment of this invention, quick disconnect/reconnect mount of this invention permits rotational movements of the probe tip while preserving sealing engagement thereof to the handset.

5 Claims, 5 Drawing Sheets

QUICK DISCONNECT FITTING FOR COUPLING INTERCHANGEABLE PROBE TIP TO LAPAROSCOPIC INSTRUMENT

This application is a continuation of U.S. application Ser. No. 07/989,109, filed Dec. 11, 1992, now abandoned, which is a continuation-in-part of application Ser. No. 07/470,771 filed on Jan. 26, 1990, now U.S. Pat. No. 5,188,591.

BACKGROUND OF THE INVENTION

1. Field of the Invention

This invention relates to a medical device. More specifically, this invention relates to a medical device for provision or delivery (infusion) of fluid and aspiration of fluid in relation to an operative field through an interchangeable probe operatively connected to such device. The interchangeable probe tip is coupled to a unique mount affixed to and/or incorporated into a handset of said device. This mount permits the rapid connection/disconnection of an interchangeable probe and freedom of orientation of the probe, relative to the handset, while preserving the sealing engagement thereof to the handset.

2. Description of the Prior Art

The provision of medical service involving surgical procedures has and continues to tax the limits of the health services industry, which includes the limited availability of skilled professionals to deliver such services and the individual's and insurer's ability/willingness to pay for extended periods of recovery in the supervised environment of a hospital. A prolonged recuperative period also causes potential economic hardship to the patient in the nature of lost earnings and exhaustion of medical benefits. Accordingly, there has and continues to be an emphasis on the delivery of health related services on an outpatient basis or by the adoption of techniques which reduce the burden on the health service industry and the patient. One such evolution has occurred in the surgical field through the implementation of "least invasive surgical" techniques (also hereinafter designed "LIS techniques" or "laparoscopy") in place of the traditional "open" or "large incision" oriented surgical procedures.

The rapid adoption and popularity of laparoscopy (surgery through micro incisions and with the aid of fiberoptics) is without precedent in modern surgical history. Surgeons throughout the world have eagerly embraced this operation, primarily because of the significant benefits in overall patient care that laparoscopic surgery offers.

Until recently, laparoscopy was performed strictly by gynecologists and not general surgeons or other specialists. During the late 1980's, this started to change when a general surgeon pioneering a new field began to perform cholecystectomy (removal of the gallbladder) laparoscopically. This technique quickly became the norm. With laparoscopic surgery gaining widespread acceptance, more and more procedures that were previously performed with conventional large, painful and temporarily disabling incisions, started being performed utilizing the laparoscopic modality. This field is still at a rapid growth rate. The need for new instruments to perform these procedures is great and the lack of such instruments is a limiting factor in the changeover from open to endoscopic surgical procedures.

Due to the lack of specifically designed instruments for general surgical laparoscopic procedures, new general surgical laparoscopists were forced to use existing gynecologic instrumentation. The predecessor to the modern medical device utilized in both laparoscopic and general surgery for infusion and aspiration of fluids were, thus, based upon devices originally designed for gynecological procedures. One instrument that was adapted for general surgical use was the "suction/irrigator." Various other electrosurgical instrumentation was also utilized. Electrosurgical instruments consisted of an insulated solid rod or hollow cannula with an exposed electrosurgical tip of several different configurations. These could be utilized to both bluntly and electrosurgically (cutting with electricity) to dissect the gallbladder from the liver bed. Electrosurgical energy can also be utilized to stop bleeding. Typically, cannula type electrosurgical instruments were equipped with one trumpet valve which was used for the evacuation of smoke (a byproduct of electrosurgery) that is created during electrosurgical dissection. The inherent protrusion of the extended tip from the electrosurgical instrument and the small internal diameter limited suction capabilities. Also, the Luer Lock connector utilized on these instruments would clog due to the Luer's small internal diameter and restrictive nature and thus waste surgical time. To switch back to a non-obstructive suction irrigation cannula was time consuming.

To satisfy the needs of the industry a symmetrical hand actuated trumpet valve which incorporated an interchangeable probe tip concept onto a laparoscopic suction/irrigator was developed. Prior to this, all suction/irrigators were one piece (the probe tip being permanently affixed to the handset or valve control body).

The instant invention as disclosed is a basic assembly which further facilitates endoscopic surgery. The invention of interchangeable, detachable probe tips is nowhere disclosed in the prior art. Because of the previous obscurity of laparoscopic surgical procedures (limited to gynecological procedures), the prior art has had little or no use for this type of instrument assembly beyond its original field of application, nor any need or incentive to modify it to accommodate a field of use that was as yet to emerge.

In order to gain perspective into the evolution of the field of laparoscopy and the techniques attendant thereto, it is initially necessary to first gain an appreciation of the instrumentation originally associated with this field. The valve body traditionally associated with laparoscopic instruments contained either two trumpet style valves or two stop cocks which were used to control suction and fluid flow. A cannula (hollow tube) was attached to the body which housed these valves. During laparoscopy, the cannula would be inserted into the abdominal cavity to enable suction and irrigation of fluids. Dependent upon physician preference, these cannula were configured either with or without holes on the tip and also were available in several lengths. A cannula with holes would enable more efficient suction of fluids and debris with less clogging. A cannula without holes allowed a physician to utilize water pressure as a dissecting force (i.e. hydrodissection) and also allowed for the suction retraction of tissue. If, during a procedure, a different tip design was necessary, the total unibodied design handpiece with cannula was changed. Luer Lock connectors (utilized in the medical field for fluid connection) allowed for this, but with this design a new suction irrigator had to be used in order to utilize a different cannula, as Luer Lock connectors are an integral part of the valve. Thus, it necessitated complete trumpet valve disconnection prior to changing probe tip/cannula design (either length or tip configuration) and turning off the irrigation source during this changing period.

The symmetrical trumpet valve concept consists of a versatile instrument for control of suction and irrigation that allows the utilization of all types of cannula and probe tips, both insulated and non-insulated in conjunction with a valve body/handset of symmetrical design. Probes with varying diameters, lengths and also electrosurgical cannula are, thus, able to be adapted to a hand-held housing which could control suction and irrigation functions. These attachments are easily and expeditiously changed without interruption of either the suction or irrigation source. In connection with this purpose a threaded connection was developed. This concept allows utilization of many different attachments to one universal body.

However, threading and unthreading attachments is not as expeditiously accomplished as is possible. Threads can be misaligned and time can be wasted during the surgical procedure as attachments are changed. Because of the foregoing limitation, new methods for quickly attaching and detaching interchangeable probe tips and attachments to the body of the trumpet valve are needed. Furthermore, in order to fulfill the demanding requirement of the laparoscopic surgeon, a quick disconnect assembly which allows for 360 degree rotation of the attachment for varied orientation of electrosurgical tips during use in the surgical environment is further required. Such preference of the clinician for freedom of orientation need occur without rotation of the body of the trumpet valve. Additional requirements of the surgeon demand that this quick disconnect fitting will accommodate five or ten millimeter outside diameter cannula probe tips or electrosurgical attachments and permit coupling to either end of the symmetrical valve.

As is evident from the foregoing discussion, the increasing adaptation of laparoscopic surgical procedures to operations traditionally requiring a large incision has introduced a whole new set of demands and specifications for the instrument designer and the surgeon for whom it is designed. Up to now, those demands have been only partially fulfilled with the introduction of the trumpet valve; and there continues to exist need for improvement thereto to further enhance the versatility and ease of use of the trumpet valve by providing greater ease and speed of interchange of probe tips to the trumpet valve body.

SUMMARY OF THE INVENTION

It is the object of this invention to remedy the above and related deficiencies in the prior art.

It is the principal object of this invention to provide an adaptor for use in conjunction with a medical device which permits the rapid attachment and disengagement of a probe to the medical device.

It is another object of this invention to provide an adaptor for rapid attachment and disengagement of a probe to a medical device, which device permits for infusion and aspiration of fluid through such probe to an operative field.

It is yet another object of this invention to provide an adaptor for rapid attachment and disengagement of an electrosurgical probe to a medical device, which device permits the delivery of electrosurgical current through said probe to an operative field.

It is still yet another object of this invention to provide an adaptor for both rapid attachment and disengagement of a probe to a medical device and the articulation of such probe, relative to the medical device, while maintaining sealing engagement thereof to the adaptor and the medical device.

Another object of this invention is to provide 360 degree rotation of electrosurgical attachments to facilitate endoscopic dissection.

Additional objects of this invention include providing a unique adaptor of this invention permanently affixed to or formed as a component of a medical device, and the user thereof in conjunction with interchangeable probe tips.

The further object of this invention is to provide a rapid and reliable method to attach and detach probe tips and electrosurgical attachments.

The above and related objects are achieved by providing, in combination, a medical device (i.e. handset) designed for use in conjunction with a probe tip and an adaptor, in operative association therewith, whereupon the adaptor provides (i) for operative and rapid engagement and disengagement thereof with one or more of the probe mounts to the medical device; or (ii) the adaptor is integral with the medical device as being integral with or permanently affixed to the valve body.

In one of the preferred embodiments of this invention, the adaptor comprises three basic or principal components; (a) a male connector for mounting of an interchangeable probe tip; (b) a female connector for mounting of the adaptor to the body of the medical device; and c) an articulating seal associated with the male connector for coupling to the probe tip. It is understood that in each of the components of the adaptor, a male connector can be used in lieu of a female connector and a female connector in lieu of a male connector consistent with the design parameters of the valve body and probe tip to which they intended to mate.

Other objects and advantages of this invention will become apparent from the following description taken in conjunction with the accompanying drawings wherein set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

The invention may be better understood by reference to the drawings in which.

DESCRIPTION OF THE PREFERRED EMBODIMENTS

Figure 1:
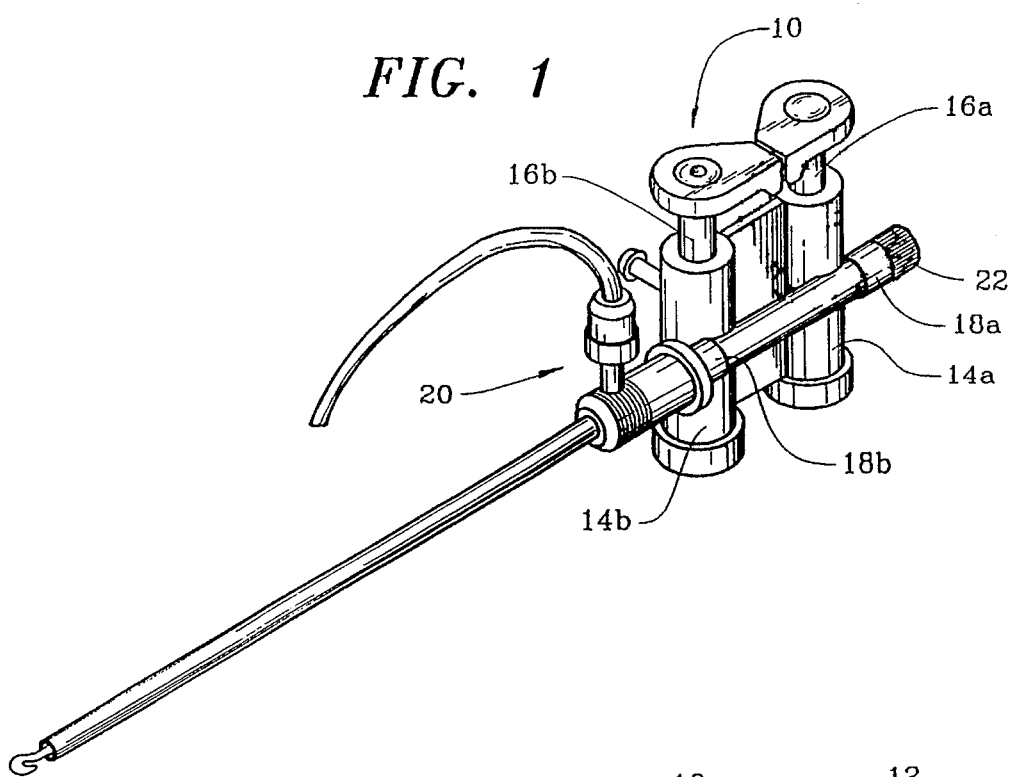
FIG. 1 is a perspective view of the medical device of the invention equipped with an interchangeable electrosurgical probe tip.

The following description is made in reference to one or more of the accompanying drawings. Where a component appears in more than one drawing, it is assigned a common reference numeral for continuity of expression and ease of understanding.

The basic configuration of the trumpet valve concept is described in co-pending application Ser. No. 07/470,771 filed Jan. 26, 1990, now U.S. Pat. No. 5,188,591 which is herein incorporated by reference in its entirety.

Figure 2:
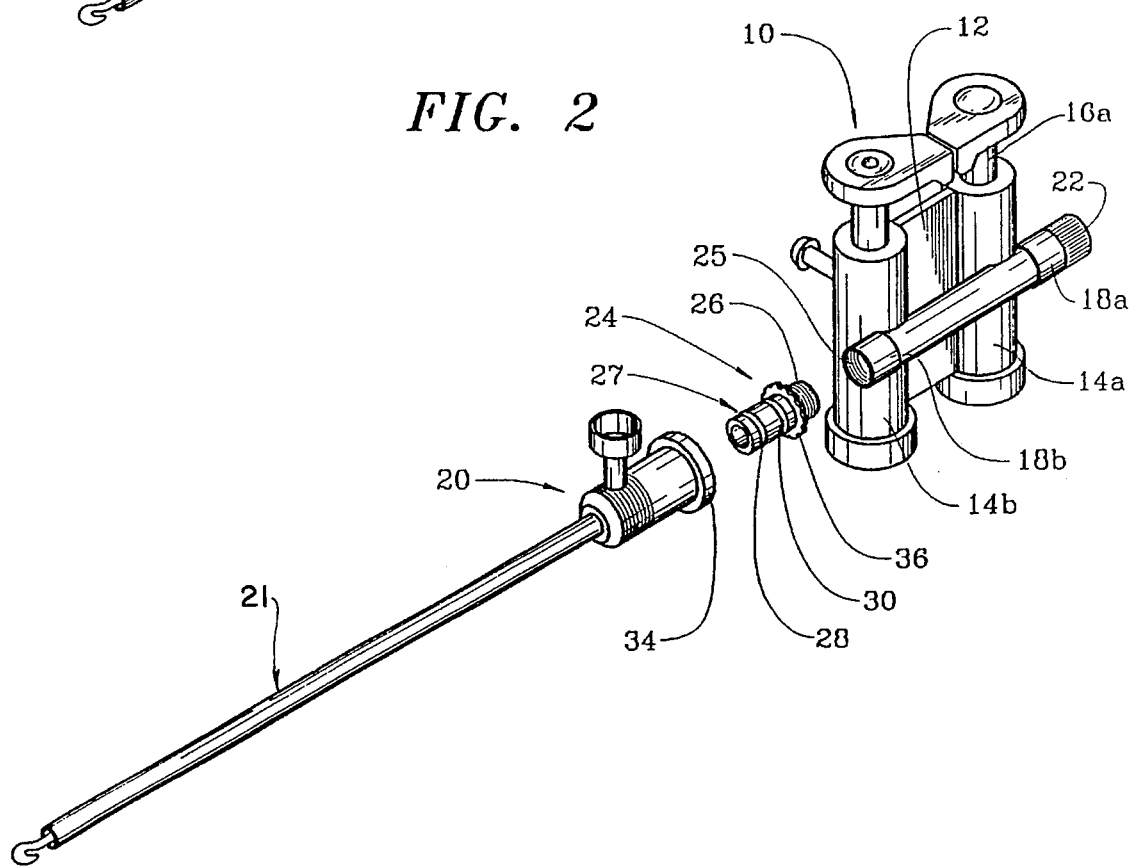
FIG. 2 is an exploded view of the medical device of FIG. 1, illustrating the individual components thereof.
Figure 3:
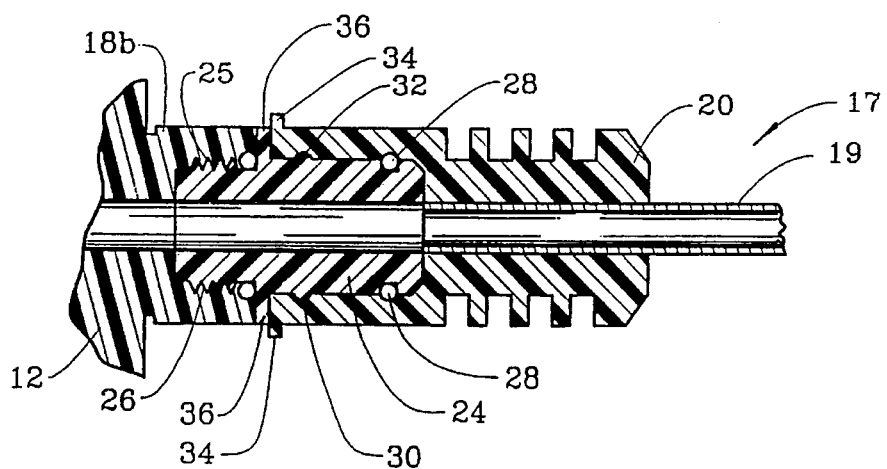
FIG. 3 is a partial section through the medical device of FIG. 1 at the junction of coupling of a probe top an the handset (trumpet valve) thereof.

FIGS. 1 through 3 illustrate a first embodiment of the improved medical device which includes a trumpet valve generally shown at 10. The valve consists of a valve housing or body 12 which defines a pair of valve chambers 14a and 14b adapted for reciprocating movement of a pair of pistons 16a and 16b. The original trumpet valve concept, as described and claimed in the above-referenced commonly assigned application/patent, is basically symmetrical in overall appearance. The basic operation of the improved trumpet valve of the present invention is essentially the same as set forth in the co-pending patent application. More specifically, trumpet valve 10 is initially connected to a source of pressurized fluid and to a source of negative pressure via a pair of fittings (not shown) which extend from the valve body. In addition, the clinician/surgeon mounts an interchangeable probe tip, generally shown at 21, onto either one or two positions 18a or 18b on valve body 12 designed for this purpose. The position not having probe tip 21 mounted thereto will have a cap 22 mounted thereto. Once valve 10 is assembled and connected to the pressurized source of fluid and negative pressure through the fittings it is ready for use.

Typically, valve 10 can be used in a hydrodissection procedure or in conjunction with other laparoscopic instruments to perform various types of biopsy or infusion of irrigation fluid to clear the operative field and thereby allow for free and unobstructive access and view.

FIG. 2 is an exploded view of the medical device of FIG. 1, illustrating the individual components thereof. More specifically, the three components of the medical device and their relationship to one another reveals the basic valve body 12 having an accepting member 25 for the acceptance and attachment of an adaptor 24. As seen in FIG. 3, accepting member 25 can be a threaded orifice or aperture defined at either or both ends of valve body 12 for receiving the first end of adaptor 24. The threaded orifice allows for threading engagement with a complimentary thread 26 of the first end of an adaptor 24. In the specific embodiment of this mating, adaptor 24 is removably but securely engaged with valve body 12. The second end of adaptor 24 is provided for operative and rapid engagement and disengagement thereof with a probe 17. The probe 17 includes a probe shaft 19 which is housed at a first end by a probe shaft attachment member 20. As seen in the drawings, attachment member 20 is a housing encompassing the first end of shaft 19 and is operatively associated with the second end of adaptor 24. When the first end of adaptor 24 is removeably secured to accepting member 25, adaptor 24 functions as a male protruding member for removable engagement with a female adaptor receiving cavity of attachment member 20. As the probe mount is easily and quickly removable from adaptor, numerous probe mounts, having various probe tip configurations and diameters, can readily be interchanged, without replacing valve body 12 and adaptor 24, for various situations which can arise during surgery.

FIG. 3 is an enlarged cross sectional view in partial of a section of trumpet valve 10 showing adaptor 24 having threads 26 and removably connected to a probe shaft attachment member 20 and to accepting member 25 on valve body 12. As adaptor 24 has threads 26 at its first end it can be used with new or existing prior art valve bodies. As seen in FIG. 3, adaptor 24 is threaded on a first end (or distal portion thereof) which is removably connected to accepting member 25 of valve body 12 and modified in a somewhat different fashion of a portion thereof which is designed for rapid coupling and de-coupling to an interchangeable probe 17 having a probe tip 21. More specifically, adaptor 24 is further provided with complimentary snap-lock seal, generally shown at 27, on the distal end thereof including means for sealing engagement with probe shaft attachment member 20 and means for snap lock engagement and disengagement at the proximal end of probe 17 with adaptor 24.

As seen in FIGS. 2 and 3 the seal 27 is in the form of a ring 28 mounted near the second end of adaptor 24. Preferably, ring 28 is constructed from silicone. The snap lock engagement/disengagement of probe shaft attachment member 20 to adaptor 24 is provided by complimentary detent, molded into adaptor collar 30 and groove 32 in the receiving cavity of attachment member 20 which mates with adaptor 24. The detent/groove combination provide for physical retention of probe shaft attachment member 20 to adaptor 24 during use and the quick release thereof when the clinician desires to interchange one probe tip for another. Furthermore, collar 34 of probe shaft attachment member 20 is shown flush against collar 36 of adaptor 24 to provide an additional seal between adaptor 24 and probe shaft attachment member 20. Collar 36 of adaptor 24 is also shown flush against the end of accepting member 25 to provide an additional seal between adaptor 24 and accepting member 25. Seal means 27, which prevents leakage of probe shaft attachment member 20 once mounted to adaptor 24, can be located on or within the probe itself in lieu of on adaptor 24 or both adaptor 24 and probe shaft attachment member 20 can contain separate yet complimentary sealing means.

As mentioned above, seal means 27 can be an o-ring 28 disposed on the outer surface portion of the second end of adaptor 24. O-ring 28 can be associated with a second groove defined by the inner surface portion of shaft attachment member 20 or can be associated with the inner surface portion of shaft attachment member 20 without the second groove. Alternatively, seal means 27 can be an o-ring 28 disposed on the inner surface portion of shaft attachment member 20. In this alternative embodiment for seal means 27, o-ring 28 is associated with a groove defined by the outer surface portion of the second end of adaptor 24 or is associated with the outer surface portion without the groove.

Though probe 17 is shown mounted to fitting 18b and cap 22 is shown fitted to fitting 18a, the invention is not limited to this configuration and probe 17 can be used mounted to fitting 18a while cap 22 is mounted to fitting 18a. Thus, the present invention can be easily used by either a right or left hand user.

Figure 5:
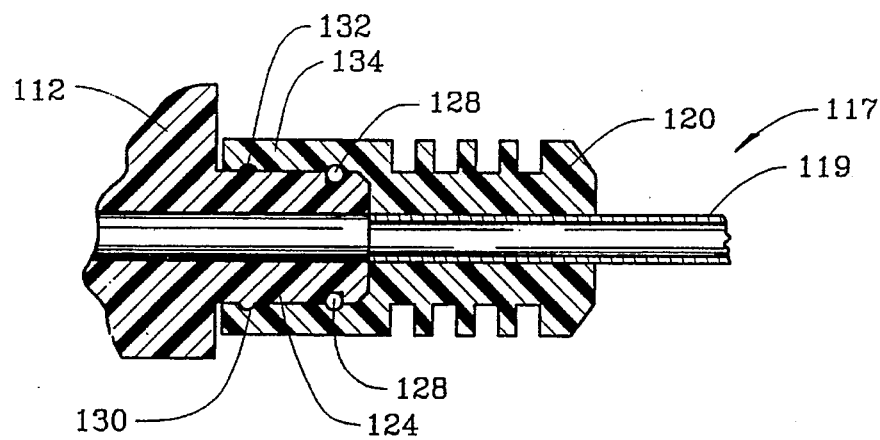
FIG. 5 is a partial section through the medical device of FIG. 4 at the junction of coupling of a probe tip and the handset (trumpet valve) thereof.
Figure 4:
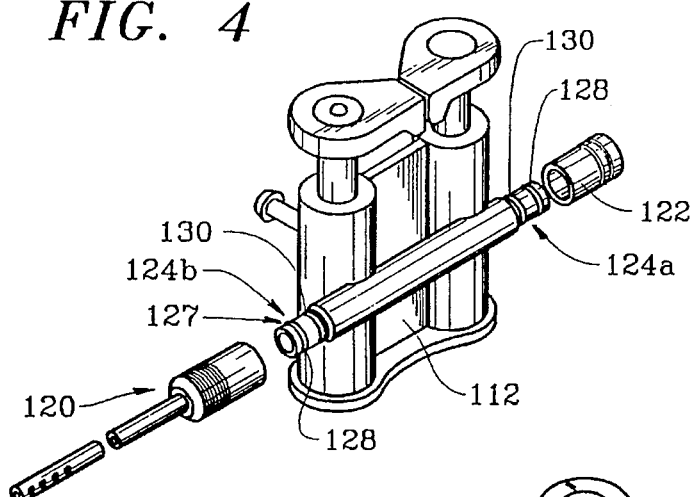
FIG. 4 is an exploded view of a second embodiment of the present invention illustrating the individual components.

FIGS. 4 and 5 illustrate a second embodiment of the present invention. In this embodiment, valve body 112 operates and is constructed similar to valve body 12 of the first embodiment with one exception. As seen in the drawings, the probe 117 includes a probe shaft 119 which is housed at a first end by a probe shaft attachment member 120. As seen in the drawings, attachment member 120 is a housing encompassing the first end of shaft 119 and is operatively associated with an exposed end of a probe mount member 124. Probe mount member 124 is a male protruding member constructed integral with valve body 112 for removable engagement with a female receiving cavity of shaft attachment member 120. In the second embodiment, probe mount member 124 is constructed integral with valve body 112. As with the first embodiment, the exposed end of probe mount member 124 is provided for operative and rapid engagement and disengagement thereof with a probe shaft attachment member 120. Probe shaft attachment member 120 is connected to probe mount member 124 essentially identical to probe shaft attachment member 20 and adaptor 24 of the first embodiment. Thus, probe mount member 124 is provided with a complimentary snap-lock seal, generally shown at 127, which includes means for sealing engagement with probe shaft attachment member 120 and means for snap lock engagement and disengagement between probe shaft attachment member 120 and probe mount member 124.

Seal means 127 can be an o-ring 128 disposed on the outer surface portion of the probe mount member 124. O-ring 128 can be associated with a second groove defined by the inner surface portion of attachment member 120 or can be associated with the inner surface portion of attachment member 120 without the second groove. Alternatively, seal means 127 can be an o-ring 128 disposed on the inner surface portion of attachment member 120. In this alternative embodiment for seal means 127, o-ring 128 is associated with a groove defined by the outer surface portion of the probe mount member 124 or is associated with the outer surface portion without the groove.

Seal 127 is in the form of a ring 128 mounted near the end of probe mount member 124. The snap lock engagement/disengagement of probe shaft attachment member 120 to probe mount member 124 is provided by complimentary detent, molded into probe mount collar 130 and groove 132 in the receiving cavity of shaft attachment member 120 which mates with of probe mount member 124 to provide for physical retention of probe shaft attachment member 120 to probe mount member 124 during use and the quick release thereof when the clinician desires to interchange one probe tip for another. Furthermore, probe shaft attachment member 120 is shown substantially encompassing the entire length of probe mount member 124 to provide an additional seal between probe mount member 124 and probe shaft attachment member 120. Seal means 127, which prevents leakage of probe shaft attachment member 120 once connected to probe mount member 124, can be located on or within the probe itself in lieu of on probe mount member 124 or both probe mount member 124 and probe shaft attachment member 120 can contain separate yet complimentary sealing means. A cap 122 is provided at the end of valve body 112 not having probe shaft attachment member 120 mounted thereto. By having the capability of mounting probe shaft attachment member 120 at either end of valve body 112, the device shown in FIGS. 4 and 5 can be used either for right or left handed use.

Figure 7:
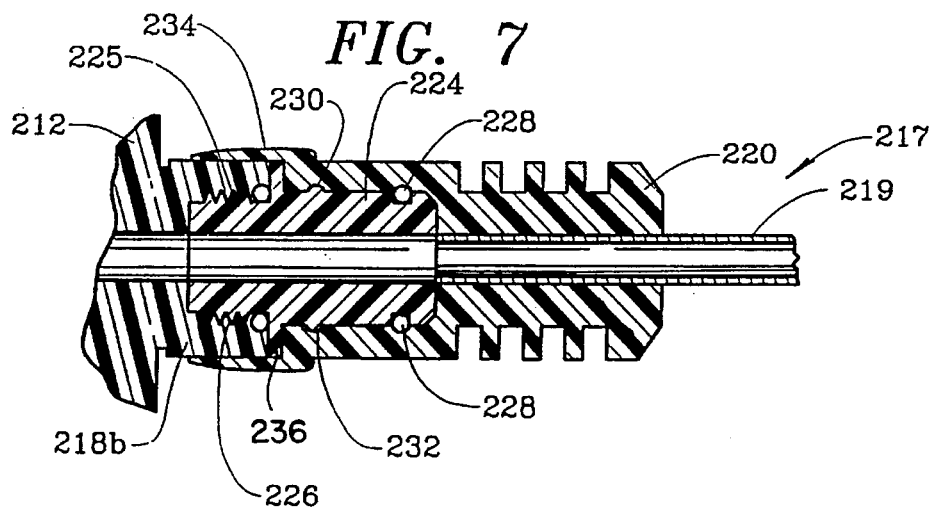
FIG. 7 is a partial section through the medical device of FIG. 6 at the junction of coupling of a probe tip and the handset (trumpet valve) thereof.
Figure 6:
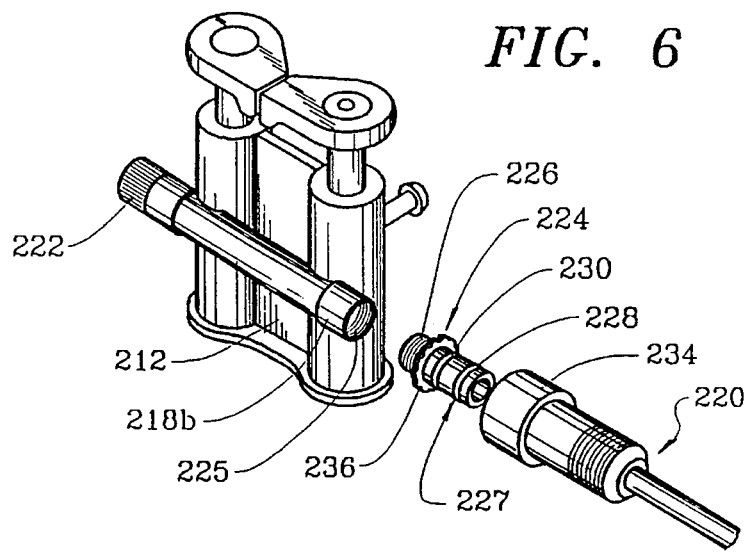
FIG. 6 is an exploded view of a third embodiment of the present invention illustrating the individual components.

FIGS. 6 and 7 illustrate a third embodiment of the present invention. In this embodiment, valve body 112 is operated and constructed similar to valve body 12 of the first embodiment. Valve body 212 includes an accepting member 225. As seen in the drawings, accepting member 225 can be a threaded orifice or aperture defined at either or both ends of valve body 212 for receiving the first end of adaptor 224. In this third embodiment, adaptor 224 is similar to adaptor 24 of the first embodiment and is removeably but securely engaged with valve body 212.

As seen in the drawings, the probe 217 includes a probe shaft 219 which is housed at a first end by a probe shaft attachment member 220. As seen in the drawings, attachment member 220 is a housing encompassing the first end of shaft 219 and is operatively associated with the second end of adaptor 224. The first end of adaptor 224 is threaded to allow for removable securement to accepting member 225 of valve body 212. When the first end of adaptor 224 is removeably secured to accepting member 225, adaptor 224 functions as a male protruding member for removable engagement with a female adaptor receiving cavity of shaft attachment member 220. The second end of adaptor 224 is provided for operative and rapid engagement and disengagement thereof with probe shaft attachment member 220.

Adaptor 224 is designed for rapid coupling and decoupling to an interchangeable probe 217. More specifically, adaptor 224 is further provided with complimentary snap-lock seal, generally shown at 227, on the proximal end thereof including means for sealing engagement with probe shaft attachment member 220 and means for snap lock engagement and disengagement at the proximal end of probe shaft attachment member 220 with adaptor 224.

Seal means 227 can be an o-ring 228 disposed on the outer surface portion of the second end of adaptor 224. O-ring 228 can be associated with a second groove defined by the inner surface portion of attachment member 220 or can be associated with the inner surface portion of attachment member 220 without the second groove. Alternatively, seal means 227 can be an o-ring 228 disposed on the inner surface portion of attachment member 220. In this alternative embodiment for seal means 227, o-ring 228 is associated with a groove defined by the outer surface portion of the second end of adaptor 224 or is associated with the outer surface portion without the groove.

Seal 227 is in the form of a ring 228 mounted near the second end of adaptor 224. The snap lock engagement/disengagement of probe shaft attachment member 220 to adaptor 224 is provided by complimentary detent, molded into adaptor collar 230 and groove 232 in the receiving cavity of probe shaft attachment member 220, which mates with adaptor 224. This, detente/groove combination provides for physical retention of the interchangeable probe 217 to adaptor 224 during use and the quick release thereof when the clinician desires to interchange one probe tip for another. Furthermore, probe shaft attachment member 220 is shown substantially encompassing the entire length of adaptor 224 and accepting member 225 to provide an additional seal between adaptor 224 and probe shaft attachment member 220. Collar 236 of adaptor 224 is also shown flush against the end of accepting member 225 to provide an additional seal between adaptor 224 and accepting member 225. Seal means 227, which prevents leakage of the interchangeable probe 217 once mounted to adaptor 224, can be located on or within probe shaft attachment member 220 itself in lieu of on adaptor 224 or both adaptor 224 and probe shaft attachment member 220 can contain separate yet complimentary sealing means. Though the interchangeable probe 217 is shown mounted to fitting 218b and cap 222 is shown fitted to fitting 218a, the invention is not limited to this configuration and the interchangeable probe 217 can be used mounted to fitting 218a while cap 222 is mounted to fitting 218b. Thus, the present invention can be easily used by either a right or left hand user.

Figure 10:
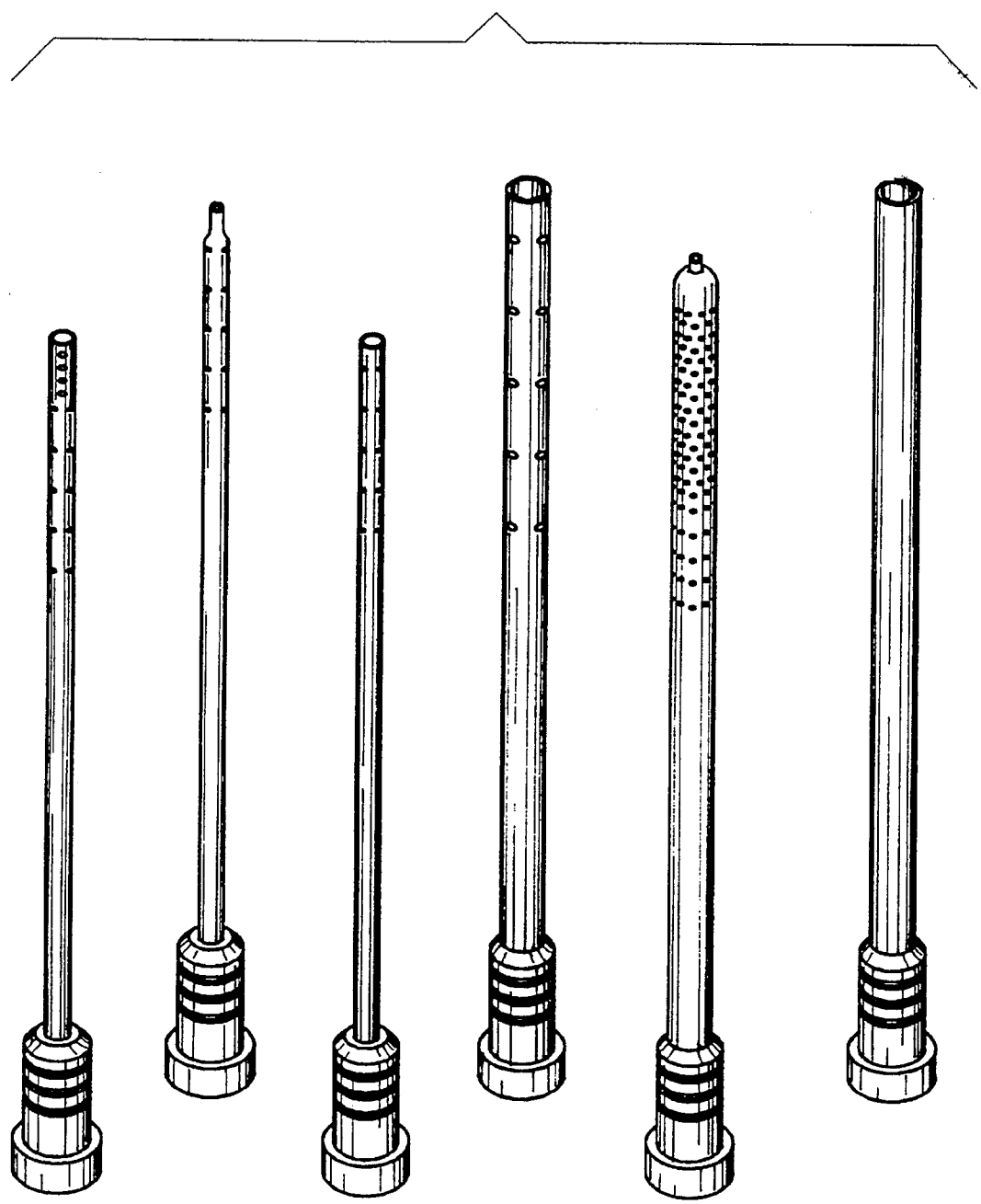
FIG. 10 is a perspective view of interchangeable suction/irrigation probes of differing shapes and orientation adapted for rapid configuration with the handset.

As the probe mount is easily and quickly removable from adaptor, numerous probe mounts, having various probe tip configurations and diameters, can readily be interchange, without replacing valve body and adaptor, for various situations which can arise during surgery. A representative sample of such interchangeable probe mounts are illustrated in FIG. 10. However, numerous other probe mounts not shown can also be used with the present invention.

Figure 8:
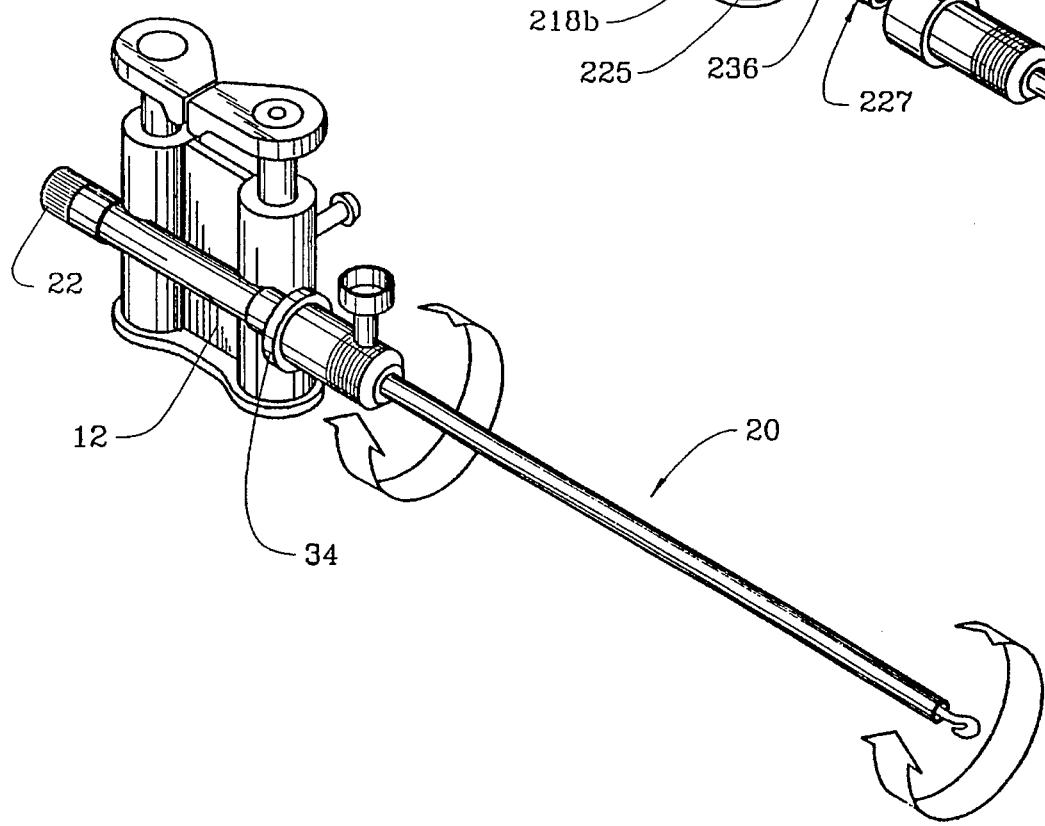
FIG. 8 is a perspective view of the medical device of FIG. 1 illustrating the freedom of rotation of the probe tip relative to the handset while maintaining sealing engagement therebetween.

FIG. 8 illustrates the articulation of electrosurgical probe in relation to the handset. Such articulation is possible due to the sealing engagement/coupling of the electrosurgical probe shaft attachment member 20 to the unique adaptor 24 of this invention. Thus, probe shaft attachment member 20 is allowed to rotate freely 360 degrees with respect to valve body 12 and adaptor 24 while retaining its sealed relationship with adaptor 24 at all times.

Figure 9:
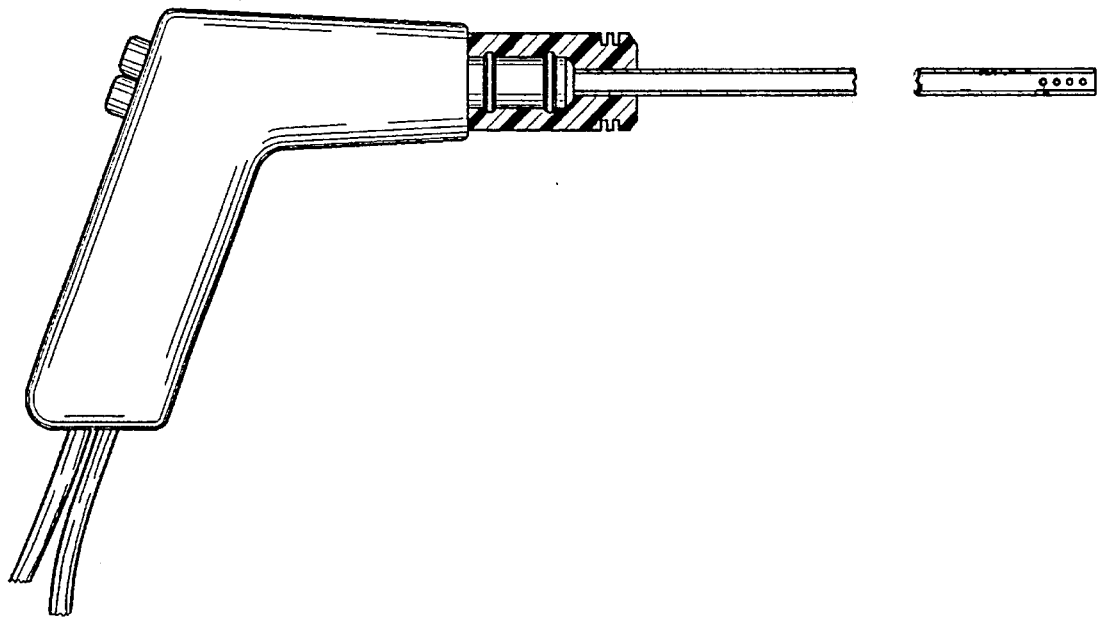
FIG. 9 is a perspective view showing a prior art pistol grip valve incorporated with the interchangeable probe capabilities of the present invention.
Figure 9A:
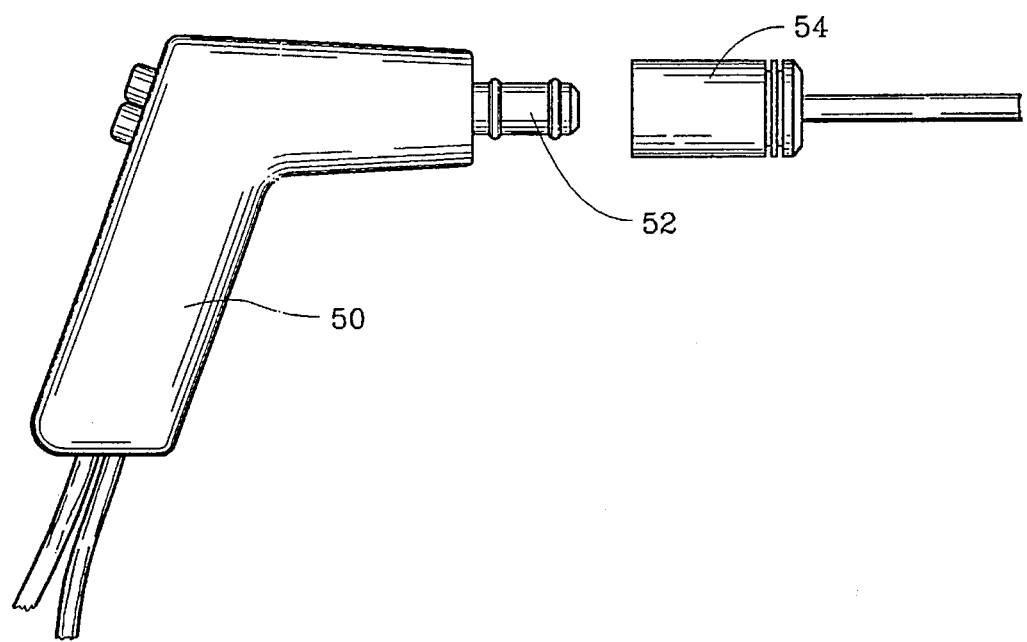
FIG. 9a is a perspective view showing the prior art pistol grip of FIG. 9 and showing a partial section view of the interchangeable probe portion of FIG. 9.

FIGS. 9 and 9a illustrates the concepts of quick disconnect probe tip of the present invention in conjunction with a prior art pistol type grip valve 50. Adaptor 52 can be removeably connected to valve 50. Alternatively, adaptor 52 is integral with or permanently affixed to valve 50. Probe 54 sealably connects to adaptor 25 in a similar manner as described above for the various embodiments shown in the drawings.

The foregoing describes a number of representative and preferred embodiments of this invention. It is not the purpose and intent of the foregoing to, however, delineate the scope of the invention which is set forth in the claims appended hereto. Further, it should be recognized that numerous other probe tip configurations and diameters, not shown herein, may also be used with the concepts of the present invention.

It is to be understood that while it has been illustrated and described certain forms of the invention, it is not to be limited to the specific forms or arrangement or parts herein described and shown. It will be apparent to those skilled in the art that various changes may be made without departing from the scope of the invention and the invention is not to be considered limited to what is shown in the drawings and described in the specification.

What is claimed is:

1. A combination surgical valve and surgical probe, said combination comprising:

a surgical probe including a probe shaft, said surgical probe further including an attachment member, said attachment member secured to said probe shaft;

a surgical valve having an inlet and an outlet;

said surgical valve further including a first probe mount member operatively associated with said outlet of said surgical valve;

said probe mount member and said attachment member operatively associated with one another, respectively, providing for rapid engagement or disengagement of said surgical probe to said surgical valve;

engaging means including a groove defined by an inner surface portion of said attachment member and a corresponding collar disposed on an outer surface portion of said probe mount member, said groove and said collar operatively associated with each other to provide a frictional engagement between said attachment member and said probe mount member; and an o-ring assembly including a notch defined by an outer surface portion of said probe mount member and a second groove defined by an inner surface portion of said attachment member, said notch and second groove housing an o-ring, when said attachment member is removeably secured to said probe mount member said o-ring assembly providing a sealed and aligned relationship between said attachment member and said probe mount member.

2. The combination surgical valve and surgical probe of claim 1 further including a second probe mount member disposed opposite of said first probe member, said first probe member and said second probe member constructed integral with said surgical valve.

3. An interchangeable probe system for use with a surgical valve assembly having an inlet and an outlet and an accepting member operatively associated with the outlet of said surgical valve, said interchangeable probe system comprising:

a surgical probe including a probe shaft and a shaft attachment member, said attachment member being secured to said probe shaft;

an adaptor means having a first end and a second end, said first end of said adaptor means being shaped for operative association with the accepting member and said second end of said adaptor means being shaped for operative association with said attachment member; and sealing means for preventing the passage of liquid between said adaptor means and said attachment member;

wherein said sealing means is an o-ring assembly including a notch defined by an outer surface portion of said second end of said adaptor means and a second groove defined by an inner surface portion of said attachment member, said notch and second groove housing an o-ring, when said attachment member is removeably secured to said second end of said adaptor means said o-ring assembly providing a sealed and aligned relationship between said attachment member and said adaptor means.

4. An interchangeable probe system for use with a surgical valve assembly having an inlet and an outlet and an accepting member operatively associated with the outlet, said interchangeable probe system comprising:

a surgical probe including a probe shaft, said surgical probe further including a shaft attachment member, said attachment member secured to said probe shaft, said attachment member having an inner surface portion defining a groove;

an adaptor means having a first end and a second end, said first end of said adaptor means being shaped for operative association with the probe accepting member and said second end of said adaptor means being shaped for operative association with said attachment member, said second end of said adaptor means having a collar disposed on an outer surface portion of said second end, said groove and said collar operatively associated with each other to provide a frictional engagement between said attachment member and said adaptor means; and an o-ring assembly to prevent the passage of liquid between said adaptor means and said attachment member, said assembly including a notch defined by an outer surface portion of said second end of said adaptor means and a second groove defined by an inner surface portion of said attachment member, said notch and second groove housing an o-ring, when said attachment member is removeably secured to said second end of said adaptor means said o-ring assembly providing a sealed and aligned relationship between said attachment member and said adaptor means.

5. The interchangeable probe system of claim 4 wherein an outer surface portion of said first end of said adaptor means has a male threaded member for mating with a threaded inner surface portion of the probe accepting member when said adaptor means is removeably secured to said receiving means.

* * * * *